United States Patent
Chen et al.

(10) Patent No.: US 10,555,979 B2
(45) Date of Patent: Feb. 11, 2020

(54) **USE OF *LACTOBACILLUS PARACASEI* GMNL-653 FOR PREPARING FOR A COMPOSITION FOR ALLEVIATING AXILLARY OSMIDROSIS**

(71) Applicant: GenMont Biotech Incorporation, Tainan (TW)

(72) Inventors: Yi-Hsing Chen, Tainan (TW); Wan-Hua Tsai, Kaohsiung (TW); Chia-Hsuan Chou, Tainan (TW); Tsuei-Yin Huang, Tainan (TW)

(73) Assignee: GENMONT BIOTECH INCORPORATION, Tainan (TW)

( * ) Notice: Subject to any disclaimer, the term of this patent is extended or adjusted under 35 U.S.C. 154(b) by 0 days.

(21) Appl. No.: 16/151,494

(22) Filed: Oct. 4, 2018

(65) Prior Publication Data

US 2019/0381118 A1 Dec. 19, 2019

(30) Foreign Application Priority Data

Jun. 19, 2018 (CN) .......................... 2018 1 0631225

(51) Int. Cl.
*A61P 17/00* (2006.01)
*A61K 9/00* (2006.01)
*A61K 35/74* (2015.01)
*A61K 35/747* (2015.01)

(52) U.S. Cl.
CPC .......... *A61K 35/747* (2013.01); *A61K 9/0014* (2013.01); *A61P 17/00* (2018.01)

(58) Field of Classification Search
None
See application file for complete search history.

(56) References Cited

FOREIGN PATENT DOCUMENTS

CN 101554389 A 10/2009

*Primary Examiner* — Padmavathi Baskar
(74) *Attorney, Agent, or Firm* — WPAT, PC

(57) ABSTRACT

Use of *Lactobacillus paracasei* for preparing for a combination for alleviating axillary osmidrosis is provided in the present invention, wherein *Lactobacillus paracasei* refers in particular to *Lactobacillus paracasei* GMNL-653, featuring abilities of aggregating and inhibiting pathogens of axillary osmidrosis for alleviation of armpit odors and presented as a topical medication or a combination of cosmetics in which fragrance is added.

8 Claims, 3 Drawing Sheets

USE OF *LACTOBACILLUS PARACASEI* GMNL-653 FOR PREPARING FOR A COMPOSITION FOR ALLEVIATING AXILLARY OSMIDROSIS

FIELD OF THE INVENTION

The present invention relates to probiotics, particularly *lactobacillus* for alleviation of axillary osmidrosis.

DESCRIPTION OF RELATED ART

Axillary osmidrosis is special odors from substances generated in reactions between secretions of sweat glands and pathogens of axillary osmidrosis. Long-chain fatty acids produced by apocrine sweat glands at armpits combine amino acids and hormones to generate less volatile and inodorous macromolecular compounds which can be degraded after reactions with pathogens of axillary osmidrosis for release of volatile and odorous micro-molecules, causing axillary osmidrosis, a common dermal disease being significant in hit sweaty days, upsetting a patient in life quality and social activities or even making a patient feel inferior and shy psychologically or stunting personality development.

The unique odors will be released after different chemical reactions are induced by distinct microbial colonies distributed at specific positions on a human body. As shown in researches, two major bacterial genus, *Staphylococcus* spp. and *Corynebacterium* spp., are distributed at armpits. In this regard, *Staphylococcus hominis* (*S. hominis*) in *Staphylococcus* spp., *Corynebacterium tuberculostearicum* in *Corynebacterium* spp. as well as *Anaerococcus* spp. are major pathogens of axillary osmidrosis.

Axillary osmidrosis has been currently treated in several different methods. The first major method is applications of skin care products. For example, antiperspirants available in the skin-care market are products developed by many manufacturers to actively block sweat pores and combining with aromatics. However, antiperspirants which are classified as the non-medicinal grade have limited effect on eliminating body odors and wear off easily by perspirations. Secondly, body fluids are not discharged from the blocked sweat pores but from other compensatory pores which probable microbial colonies also emit undesirable odors. Thirdly, a person who applied antiperspirants on skin may suffer from sunstroke when body heat is not dissipated from perspirations. Fourthly, timing of using antiperspirants which should be applied or sprayed the night before is limited and not effective immediately.

The second major method is the surgical operation through which apocrine sweat glands are removed for neither glandular secretion nor axillary osmidrosis. However, in contrast to skin care products such as antiperspirants, the surgical operation has a tremendous higher cost, and surgical wounds will require a period of time for healing.

"Botulinus toxin composition and preparation method thereof" disclosed in Chinese Patent Number CN 101554389 discloses a composition and a method applied to treatment or prevention of diseases such as the over-strengthening function of skin glands or armpit odors. The method introduced in the patent is to inhibit transmission of media at tele neurons and excessive secretions of skin glands. However, botulinus toxin with neurotoxicity is adverse to nerve conduction and should not be administered to a user for a long term, which may risk side effects of perspiration anomaly when overdosed.

Accordingly, it is desired to settle the above drawbacks with respect to skin care products and surgical operations by providing an effective method for no adverse effect on sweat glands and the neurotransmitter system but safe treatment deserve to be studied by the persons skilled in the art.

SUMMARY OF THE INVENTION

Having considered deficiencies and/or drawbacks in the prior art and studied an innovative technique in experiments for several years; the present invention provides the use of *Lactobacillus paracasei* GMNL-653 for preparing for a composition for alleviating axillary osmidrosis.

Use of *Lactobacillus paracasei* GMNL-653 for preparing for a composition for alleviating axillary osmidrosis in the present invention are characteristic of avoiding problems and/or risks in the existing methods for improvement of axillary osmidrosis and *Lactobacillus paracasei* GMNL-653 was deposited in China Center for Type Culture Collection (Deposit No.: CCTCC M 2016226).

The probiotics, particularly specific probiotics rather than all strains, inhibits pathogens of axillary osmidrosis for alleviation of armpit odors and is different from the traditional method focusing on sweat glands and nerve conduction currently. In this regard, *Lactobacillus paracasei* GMNL-653, live or heat-killed, aggregating and inhibiting *Staphylococcus hominis*, the pathogens of axillary osmidrosis, can be easily applied to a patient with armpit odors for alleviating bacterial colonies of pathogens of axillary osmidrosis through direct contacts of pathogens.

The probiotic, *Lactobacillus paracasei* GMNL-653 has no adverse invention concerns in safety and has no adverse effect on sweat glands or the neurotransmitter system. Unlike the traditional method, the probiotic, *Lactobacillus paracasei* GMNL-653 triggers no side effects such as blockage of sweat glands and sunstroke. With the ability to aggregate *Staphylococcus hominis* within a short period of time, *Lactobacillus paracasei* GMNL-653 works quickly without the drawback of the conventional skin care products applied on skin the night before. As a non-invasive application comparing to the high-cost plastic surgeries, the instant invention has no issues in regarding wound healing and incomplete axillary osmidrosis alleviation. Moreover, the effect on pathogens of axillary osmidrosis disclosed herein is available in live or heat-killed GMNL-653 and flexible in manufacturing processes as well as applications in contrast to traditional probiotics which should be kept alive in use.

In Embodiment 1 of the present invention, the probiotic of *Lactobacillus paracasei* GMNL-653 with the best coaggregation ability to aggregate *Staphylococcus hominis* in pathogens of axillary osmidrosis was selected through the coaggregation test.

In Embodiment 2 of the present invention, *Lactobacillus paracasei* GMNL-653, live or heat-killed, had the coaggregation ability to aggregate *Staphylococcus hominis*, as shown in test results.

In Embodiment 3 of the present invention, the positive correlations between *Lactobacillus paracasei* GMNL-653 in various dosages and the effect of aggregating *Staphylococcus hominis* were demonstrated.

In Embodiment 4 of the present invention, the strong interactions between *Lactobacillus paracasei* GMNL-653 and *Staphylococcus hominis* as shown in coaggregation phenomena were demonstrated in Scanning Electron Microscope (SEM) photos.

In Embodiment 5 of the present invention, *Lactobacillus paracasei* GMNL-653 with the coaggregation ability to *Staphylococcus hominis* was also able to inhibit growth of *Staphylococcus hominis*, as shown in the test of inhibition zone.

In the present invention, *Lactobacillus paracasei* GMNL-653, which aggregated and inhibited pathogens of axillary osmidrosis, could be prepared as a topical medication or a combination of cosmetics for alleviation of axillary osmidrosis. Different from defective traditional methods, skin care products or plastic surgeries, available to users with armpit odors for a long period of time, the applications based on probiotics, live or heat-killed, first disclosed for alleviation of axillary osmidrosis herein are brand new and innovative in concept and flexible in widespread commercial values.

DETAILED DESCRIPTION OF THE INVENTION

Figure 1A:
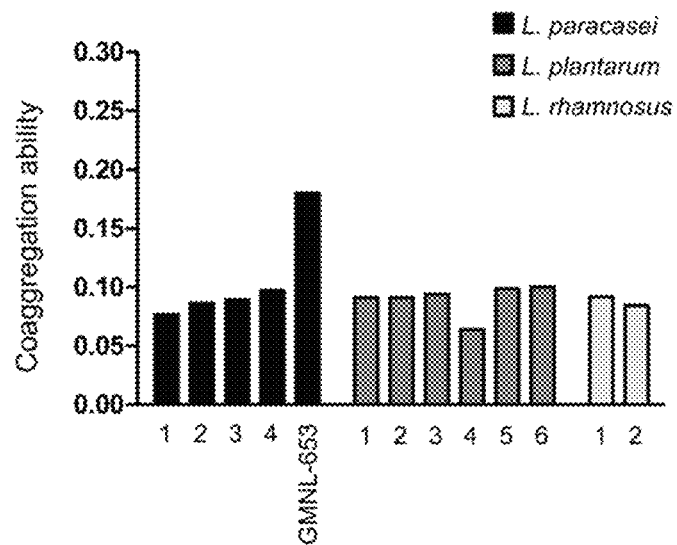
FIG. 1A illustrates a probiotic with the best coaggregation ability to aggregate *Staphylococcus hominis* BCRC 12156 was selected.

The present application is introduced in the following embodiments in which a safe and effective method is provided by the patent applicant for alleviation of axillary osmidrosis, no adverse effect on sweat glands and the neurotransmitter system, and no drawbacks of existing skin care products and/or plastic surgeries.

The present application is disclosed in but not limited to the following embodiments; any modification or revision based on general knowledge without departing the spirit and scope of the present invention should be incorporated in claims hereinafter.

Unless otherwise specified, all materials used in the present invention are available in the market, and *Lactobacillus paracasei* GMNL-653 was deposited in the Bioresource Collection and Research Center of Food Industry Research and Development Institute (BCRC of FIRDI) with Deposit No.: BCRC 910721 and the China Center for Type Culture Collection (CCTCC) with Deposit No.: CCTCC M 2016226. The definitions of terms in the present invention are shown as follows: "colony forming units/ml; cfu/ml" means the total number of bacterial colonies per millimeter of broth; "OD (optical density) 600" means the optical density of solutions at the wavelength of 600 nm for the estimation of the concentration of bacterial broth; "OD 595" means the optical density of solution at the wavelength of 595 nm.

Embodiment 1: Coaggregation Abilities of Selected Probiotics to Aggregate Pathogens of Axillary Osmidrosis For coaggregation of pathogens of axillary osmidrosis and probiotics, three representative species of probiotics including *Lactobacillus paracasei* (*L. paracasei* for short), *Lactobacillus plantarum* (*L. plantarum* for short) and *Lactobacillus rhamnosus* (*L. rhamnosus* for short) were selected and some bacterial strains were further collected from each of the three species for preparations of probiotic strains in the coaggregation test.

The process of culturing probiotic strains is shown as follows. Bacterial strains had been inoculated in 1 ml MRS broth (Lactosebacillus Broth acc. to DE MAN, ROGOSA and SHARPE) from frozen tubes and rested under aerobic conditions at 37° C. in the next 20 hours; 10 ul bacterial broth (1% of the broth volume) was added into 1 ml MRS broth for secondary activation and rested under aerobic conditions at 37° C. in the next 20 hours. OD600 of bacterial broths was measured with a spectrophotometer for estimation of the total number of bacterial colonies; the concentration of bacterial broth was adjusted and kept at $2 \times 10^9$ cfu/ml by PBS (Phosphate Buffered Saline) for later uses.

For culturing of pathogens of axillary osmidrosis, the numbers of two bacterial strains, both of which were classified as *Staphylococcus hominis* (*S. hominis* for short), in Embodiment 1 were BCRC12156 (subspecies: *hominis*) and BCRC17959 (subspecies: *novobiosepticus*). Based on the four-quadrant sequential streaking method, BCRC12156 and BCRC17959 were cultured in TSA (Tryptone Soy Agar) growth media and TSA growth media with 5% defibrinated sheep blood, respectively. After two bacterial strains had been cultured under aerobic conditions at 37° C. for 24 hours, several single colonies were chosen for secondary activation by the streaking method and cultured under aerobic conditions at 37° C. in the next 24 hours. Finally, the microbial content of bacterial colonies, which had been scraped from the streak plate and suspended in PBS, was measured with a spectrophotometer for OD600 and the concentration of bacterial broth was adjusted and kept at $2 \times 10^9$ cfu/ml for later uses.

The process of the coaggregation test after preparations of probiotics and pathogens of axillary osmidrosisis presented hereinafter. 0.5 ml probiotics and 0.5 ml pathogens of axillary osmidrosis, each of which had a proper concentration, were mixed to prepare for a reaction group. In the control groups, 0.5 ml probiotics in which 0.5 ml PBS were added were prepared for the pure probiotics group and 0.5 ml pathogens of axillary osmidrosis in which 0.5 ml PBS were added were prepared for the pure pathogen group. The coaggregation phenomena of mixtures in all groups, which had rested for 20 minutes, were observed and the upper part of a mixture presenting strong coaggregation was limpid. The coaggregation ability was observed in 100 μl mixtures at the upper part of each tube based on OD595 and the high coaggregation ability was presented by high OD595 of the formula (formula: coaggregation ability=OD595 of the pure pathogen group+OD595 of the pure probiotics group−OD595 of the reaction group).

Figure 1B:
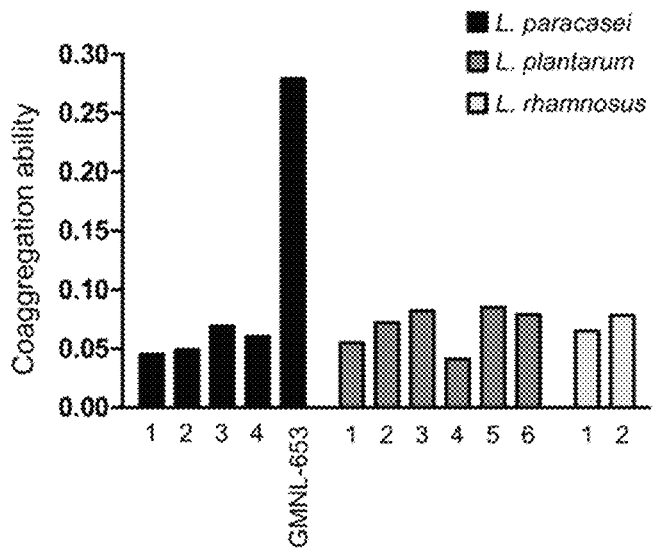
FIG. 1B illustrates a probiotic with the best coaggregation ability to aggregate *Staphylococcus hominis* BCRC 17959 was selected.

The test results as shown in FIGS. 1A and 1B provide that *Lactobacillus paracasei* GMNL-653 (hereinafter referred to as GMNL-653) presents the best coaggregation ability among all tested probiotics including *Lactobacillus plantarum*, *Lactobacillus rhamnosus* and other bacterial strains of

*Lactobacillus paracasei*. Accordingly, the good coaggregation ability peculiar to GMNL-653 is not observed in all probiotics.

Embodiment 2: Coaggregation Ability of Live or Heat-Killed *Lactobacillus paracasei* GMNL-653 to Aggregate Pathogens of Axillary Osmidrosis The coaggregation abilities between live GMNL-653 and heat-killed GMNL-653 to aggregate pathogens of axillary osmidrosis were compared for clarifying the question if the coaggregation ability of live GMNL-653 only was applicable to aggregating pathogens of axillary osmidrosis.

The culturing of live GMNL-653 and pathogens of axillary osmidrosis (from *Staphylococcus hominis* BCRC12156 and BCRC17959) has been presented in Embodiment 1. The culturing of heat-killed GMNL-653 is shown as follows. The bacterial broth with live GMNL-653, which had been prepared and kept at the concentration of $2 \times 10^9$ cfu/ml, was processed in the autoclaved sterilization at 121° C. in the next 15 minutes for preparation of heat-killed GMNL-653 to be used later.

As shown in Embodiment 1 for preparation of the control group, live GMNL-653 and heat-killed GMNL-653, each of which had the concentration of $2 \times 10^9$ cfu/ml, were mixed with pathogens of axillary osmidrosis for the coaggregation test through which the coaggregation ability was determined, respectively.

Figure 2:
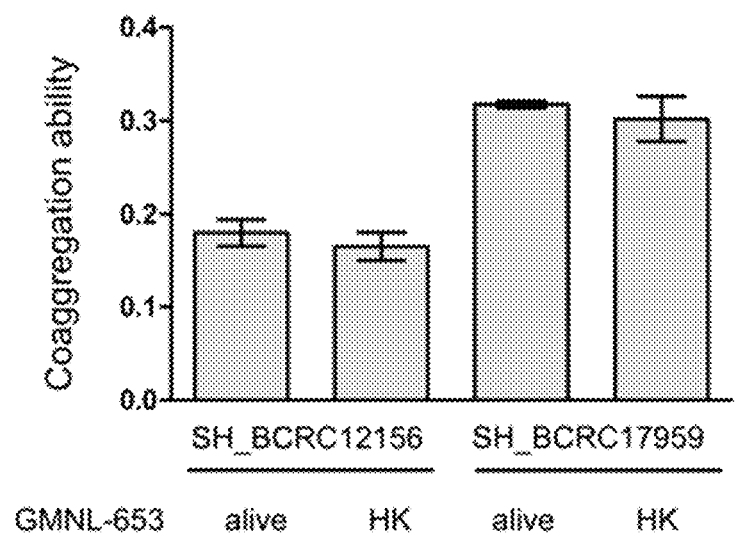
FIG. 2 illustrates the coaggregation abilities of live and heat-killed *Lactobacillus paracasei* GMNL-653 to aggregate *Staphylococcus hominis* were compared.

The test results as shown in FIG. 2 provide that that the coaggregation abilities of both live GMNL-653 and heat-killed GMNL-653 were applicable to and presented no difference in aggregating *Staphylococcus hominis* BCRC12156 and BCRC17959. Accordingly, the heat-killing process had less association to do with the interaction between GMNL-653 and *Staphylococcus hominis* BCRC12156 (BCRC17959).

Embodiment 3: Coaggregation Abilities of Heat-Killed GMNL-653 in Various Dosages to Aggregate Pathogens of Axillary Osmidrosis As shown in steps in Embodiment 2 for culturing of heat-killed GMNL-653 and pathogens of axillary osmidrosis, live GMNL-653 with the concentration of $2 \times 10^{10}$ cfu/ml before the heat-killing step in Embodiment 3 were processed in the autoclaved sterilization for preparing heat-killed GMNL-653 and clarifying the question that the coaggregation ability of GMNL-653 to aggregate *Staphylococcus hominis* was positively correlated with the dosage of GMNL-653. Then, three adjusted concentrations of heat-killed GMNL-653, that is, $1 \times 10^9$, $2 \times 10^9$ and $2 \times 10^{10}$ cfu/ml, were prepared for later uses in the coaggregation test as shown in the previous embodiment and comparisons in the coaggregation abilities of GMNL-653 in different dosages to aggregate *Staphylococcus hominis* BCRC12156 and BCRC17959.

Figure 3:
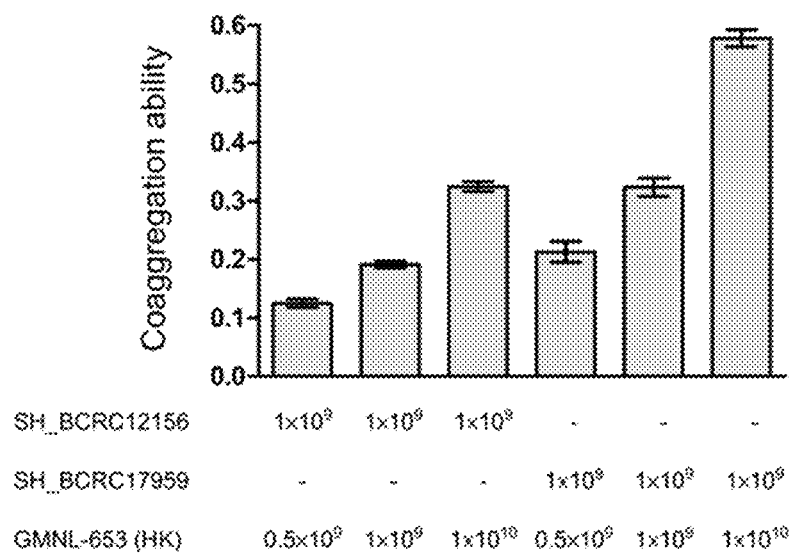
FIG. 3 illustrates the coaggregation abilities of heat-killed *Lactobacillus paracasei* GMNL-653 in various dosages to aggregate *Staphylococcus hominis* were compared.

The test results as shown in FIG. 3 provide that the significantly positive correlations between the coaggregation ability of GMNL-653 to aggregate *Staphylococcus hominis* and the dosages of GMNL-653 from $0.5 \times 10^9$ to $1 \times 10^{10}$ were observed. Accordingly, more pathogens of axillary osmidrosis could be removed by GMNL-653 in a higher dosage.

Embodiment 4: Strong Interactions Between GMNL-653 and Pathogens of Axillary Osmidrosis Shown in SEM Photos The interactions between *Lactobacillus paracasei* GMNL-653 and *Staphylococcus hominis* were further checked in Embodiment 4. After some droplets of bacterial broths of the reaction group in the previous coaggregation test were instilled onto a coverslip, a glass slide, the coverslip, a piece of bibulous paper and a funnel, all of which were stacked sequentially and bundled by a rubber band at two ends, had been centrifuged at 800 rpm for five minutes such that the bacterial broth adhered to the coverslip. 1 ml of 2.5% glutaraldehyde was added on the coverslip at a 24-well cell culture plate for fixing at room temperature in the next one hour. Then, the coverslip was rinsed in PBS for three 5-minute cycles; the coverslip acted sequentially with 40%, 75% and 95% ethyl alcohol in the next 10 minutes each time and 100% ethyl alcohol in the next 20 minutes for three cycles totally until dehydration. Finally, the coverslip was coated with a metal film and observed by SEM (Hitachi 3000n).

Figure 4:
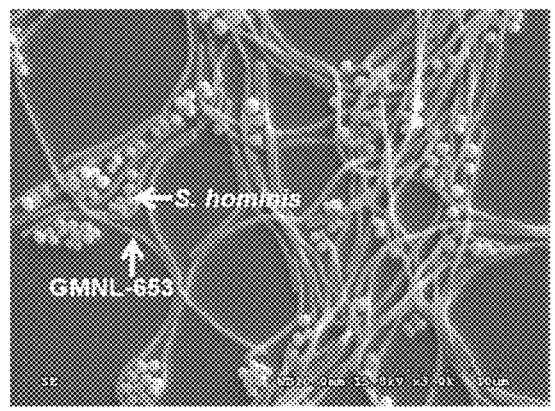
FIG. 4 illustrates coaggregation phenomena of *Staphylococcus hominis* and *Lactobacillus paracasei* GMNL-653 demonstrated in Scanning Electron Microscope (SEM).

The test results as shown in FIG. 4 provide that GMNL-653 and *Staphylococcus hominis* having co-aggregated and twined around each other displayed strong interaction, which meant pathogens of axillary osmidrosis were removed by GMNL-653 through coaggregation.

Embodiment 5: The Ability of GMNL-653 to Inhibit Growth of Pathogens of Axillary Osmidrosis In addition to the coaggregation ability of GMNL-653 to aggregate *Staphylococcus hominis*, the ability of GMNL-653 to create an inhibition zone around *Staphylococcus hominis* was observed.

As shown in Embodiment 1 for culturing of probiotics and pathogens of axillary osmidrosis, probiotics were selected from *Lactobacillus casei* (*L. casei*), *Lactobacillus paracasei* GMNL-653, *Lactobacillus reuteri* (*L. reuteri*) and *L. rhamnosus* and pathogens of axillary osmidrosis were *Staphylococcus hominis* BCRC17959. The concentrations of cultured probiotics and pathogens of axillary osmidrosis were $5 \times 10^9$ cfu/ml and $1 \times 10^9$ cfu/ml, respectively.

The inhibition zone was tested in Embodiment 5. $1 \times 10^8$ cfu bacterial broth in prepared pathogens of axillary osmidrosis was spread on solid media uniformly. The solid media was compressed by an 11 mm glass tube for creations of pores, each of them was filled with 200 μL bacterial broth for 24-hour and 48-hour incubation during which the diameter of an inhibition zone was checked with an electronic vernier caliper (inhibition zone's diameter=outer diameter-inner diameter).

Figure 5:
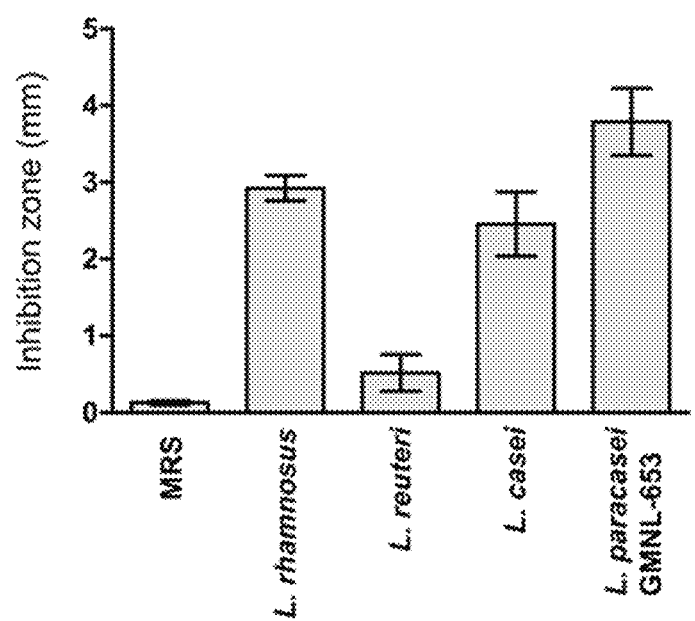
FIG. 5 illustrates the abilities of probiotics to inhibit *Staphylococcus hominis*.

The test results as shown in FIG. 5 provide that GMNL-653, which did better in inhibiting *Staphylococcus hominis* than other three probiotics, presented a good ability to aggregate and suppress pathogens of axillary osmidrosis and not all of probiotics performed well in inhibiting pathogens of osmidros is like GMNL-653.

As shown in above embodiments, GMNL-653 with the ability to inhibit pathogens of axillary osmidrosis relies on interactions between surface molecules of GMNL-653 and pathogens of axillary osmidrosis to create complexes through a coaggregation process for eliminating and suppressing pathogens.

Compared with other probiotics being screened, GMNL-653 has the better coaggregation ability that was verified in the coaggregation tests in embodiments. Moreover, either live GMNL-653 or heat-killed GMNL-653 can coaggregate pathogens of axillary osmidrosisas shown in the embodiment, that is, a heat-killing process had less effect on interactions between GMNL-653, live or heat-killed, and pathogens of axillary osmidrosis; the coaggregation effect was promoted with the dosage of GMNL-653 increased, as shown in SEM photos. In addition to the coaggregation effect, another advantage of GMNL-653 to inhibit growth of pathogens of axillary osmidrosis directly was also observed. Among the tested probiotics, GMNL-653 has the better effects of co-aggregating and inhibiting pathogens of axillary osmidrosis, the distinct function of the strain, which was a major feature in the present invention.

For alleviation of axillary osmidrosis, GMNL-653 can be further prepared as a combination for a patient with body odors, for example, treatment of microbial colonies at a patient's armpits and elimination or coaggregation of pathogens of axillary osmidrosis.

Furthermore, GMNL-653, live or heat-killed, is good in eliminating pathogens of axillary osmidrosis and flexibly prepared as topical medication, differing from the oral form common in pharmaceutical formulations of most probiotics, applied on armpits for direct alleviation of axillary osmidrosis is effectively. Accordingly, GMNL-653 works as either a topical medication or a cosmetic.

In the present invention, GMNL-653 can be prepared as a combination for alleviating axillary osmidrosis such as topical medication and cosmetic in which fragrance is added without safety concerns in applications compared with existing skin care products for prevention of axillary osmidrosis that has some drawbacks of affecting sweat glands or the neurotransmitter system or being non-concurrent. Moreover, GMNL-653, live or heat-killed, is characteristic of consistent efficiency without problems of high-cost plastic surgeries, wound healing, axillary osmidrosis treated incompletely, or restriction in preservation of live microbial colonies. Because of flexible manufacturing processes and applications, GMNL-653 is a brand new, hazard-free, safe and effective product for alleviation of axillary osmidrosis in the existing skin care market.

In summary, use of *Lactobacillus paracasei* GMNL-653 for preparing for a combination for alleviating axillary osmidrosis, which are innovative work in technical ideas and feature several effects in contrast to conventional methods, meet novelty and non-obviousness for patentability.

What is claimed is:

1. A method used for alleviating axillary osmidrosis, comprising administrating a probiotic composition, wherein the probiotic bacterial strain includes *Lactobacillus paracasei* GMNL-653 with the deposition number of CCTCC M 2016226.

2. The method as claimed in claim 1, wherein the *Lactobacillus paracasei* GMNL-653 is live and/or dead.

3. The method as claimed in claim 1, wherein heat-killed *Lactobacillus paracasei* GMNL-653 is derived in a heat-killed process.

4. The method as claimed in claim 1, wherein the *Lactobacillus paracasei* GMNL-653 possesses abilities to aggregate and inhibit pathogens of axillary osmidrosis.

5. The method as claimed in claim 4, wherein the pathogens of axillary osmidrosis are *Staphylococcus hominis*.

6. A topical medication for alleviating axillary osmidrosis, comprising *Lactobacillus paracasei* GMNL-653 with the deposition number of CCTCC M 2016226 and possessing abilities to aggregate and inhibit pathogens of axillary osmidrosis, wherein the topical medication comprising medical accepted carriers; wherein the topical medication presented as a medical patch, a liquid medicine, a balm, medical oils, medical powders, gels, sprays or a combination thereof.

7. A cosmetic combination for alleviating axillary osmidrosis, comprising *Lactobacillus paracasei* GMNL-653 with the deposition number of CCTCC M 2016226 and possessing abilities to aggregate and inhibit pathogens of axillary osmidrosis, wherein the cosmetic combination presented for topical uses; wherein the cosmetic combination comprising formulations of aqueous solutions, creams, pastes, solid agents, powders, gels, emulsions, lotions, emulsion pastes, rollers, sprays or surgical dressings.

8. The cosmetic combination as claimed in claim 7, further comprising fragrance.

* * * * *